United States Patent
Gao et al.

(10) Patent No.: US 11,851,704 B2
(45) Date of Patent: *Dec. 26, 2023

(54) DEEPSIMULATOR METHOD AND SYSTEM FOR MIMICKING NANOPORE SEQUENCING

(71) Applicant: KING ABDULLAH UNIVERSITY OF SCIENCE AND TECHNOLOGY, Thuwal (SA)

(72) Inventors: Xin Gao, Thuwal (SA); Yu Li, Thuwal (SA); Sheng Wang, Thuwal (SA); Renmin Han, Thuwal (SA)

(73) Assignee: KING ABDULLAH UNIVERSITY OF SCIENCE AND TECHNOLOGY, Thuwal (SA)

( * ) Notice: Subject to any disclaimer, the term of this patent is extended or adjusted under 35 U.S.C. 154(b) by 185 days.

This patent is subject to a terminal disclaimer.

(21) Appl. No.: 17/355,823

(22) Filed: Jun. 23, 2021

(65) Prior Publication Data
US 2021/0317523 A1  Oct. 14, 2021

Related U.S. Application Data

(63) Continuation of application No. 16/769,127, filed as application No. PCT/IB2018/058502 on Oct. 30, 2018, now Pat. No. 11,078,531.
(Continued)

(51) Int. Cl.
*G01N 33/48* (2006.01)
*G01N 33/50* (2006.01)
(Continued)

(52) U.S. Cl.
CPC .......... *C12Q 1/6869* (2013.01); *G06N 3/088* (2013.01); *G16B 30/20* (2019.02); *G16B 40/10* (2019.02); *G16B 40/30* (2019.02)

(58) Field of Classification Search
CPC ...... C12Q 1/6869; G06N 3/088; G16B 30/20; G16B 40/10; G16B 40/30
See application file for complete search history.

(56) References Cited

U.S. PATENT DOCUMENTS 11,078,531 B2 * 8/2021 Gao ...................... G16B 40/10

FOREIGN PATENT DOCUMENTS

WO  2013041878 A1  3/2013
WO  2016181369 A1  11/2016

OTHER PUBLICATIONS

Boufounos et al. Basecalling using hidden Markov models. Journal of the Franklin Institute. vol. 341, pp. 23-36. (Year: 2004).*
(Continued)

*Primary Examiner* — Russell S Negin
(74) *Attorney, Agent, or Firm* — PATENT PORTFOLIO BUILDERS PLLC

(57) ABSTRACT

A method for sequencing biopolymers. The method includes selecting with a sequence generator module an input nucleotide sequence having plural k-mers; simulating with a deep learning simulator, actual electrical current signals corresponding to the input nucleotide sequence; identifying reads that correspond to the actual electrical current signals; and displaying the reads. The deep learning simulator includes a context-dependent deep learning model that takes into consideration a position of a k-mer of the plural k-mers on the input nucleotide sequence when calculating a corresponding actual electrical current.

20 Claims, 8 Drawing Sheets

Related U.S. Application Data

(60) Provisional application No. 62/702,161, filed on Jul. 23, 2018, provisional application No. 62/599,908, filed on Dec. 18, 2017, provisional application No. 62/598,086, filed on Dec. 13, 2017.

(51) Int. Cl.
  *C12Q 1/6869* (2018.01)
  *G16B 40/30* (2019.01)
  *G16B 40/10* (2019.01)
  *G16B 30/20* (2019.01)
  *G06N 3/088* (2023.01)

(56) References Cited

OTHER PUBLICATIONS

"Disease Watch," In the News, Nature Reveiws, Microbiology, Feb. 2009, vol. 7, pp. 96-97.
Abadi, M., "TensorFlow: Learning Functions at Scale," Sep. 18-24, 2016, Acm Sigplan Notices, vol. 51, No. 9, 1 page.
Abnizova, I., et al., "Analysis of Context-Dependent Errors for Illumina Sequencing," Journal of Bioinformatics and Computational Biology, Apr. 1, 2012, vol. 10, No. 2 (20 pages).
Akaike, H., "Canonical Correlation Analysis of Time Series and the Use of an Information Criterion," Mathematics in Science and Engineering, 1976, vol. 126, pp. 27-96.
Alipanahi, B., et al., "Predicting the Sequence Specificities of DNA- and RNA-Binding Proteins by Deep Learning," National Biotechnology, Aug. 2015, vol. 33, No. 8, pp. 831-838.
Altschul, S.F., et al., "Gapped BLAST and PSI-BLAST: A New Generation of Protein Database Search Programs," Nucleic Acids Research, Sep. 1, 1997, vol. 25, No. 17, pp. 3389-3402.
Baker, E.A.G., "Silico: A Simulator of Long Read Sequencing in PacBio and Oxford Nanopore," bioRxiv, Sep. 22, 2016, pp. 76901-76903.
Boza, V., et al., "Deepnano: Deep Recurrent Neural Networks for Base Calling in Minion Nanopore Reads," PLoS One, Jun. 5, 2017, vol. 12, No. 6, 13 pages.
Byrne, A., et al., "Nanopore Long-Read RNAseq Reveals Widespread Transcriptional Variation Among the Surface Receptors of Individual B Cells," Nature Communications, Jul. 19, 2017, 11 pages.
Dai, H., et al., "Sequence2Vec: A Novel Embedding Approach for Modeling Transcription Factor Binding Affinity Landscape," Bioinformatics, Jul. 26, 2017, vol. 33, No. 2, pp. 3575-3583.
David, M., et al., "Nanocall: An Open Source Basecaller for Oxford Nanopore Sequencing Data," Bioinformatics, Sep. 10, 2016, Vo. 33, No. 1, pp. 49-55.
Deamer, D., et al., "Three Decades of Nanopore Sequencing," Nature Biotechnology, May 2016, vol. 34, No. 5, pp. 518-525.
Delcher, A. L., et al., "Alignment of Whole Genomes," Nucleic Acids Research, Apr. 14, 1999, vol. 27, No. 11, pp. 2369-2376.
Escalona, M., et al., "A Comparison of Tools for the Simulation of Genomic Next-Generation Sequencing Data," Nature Reviews, Genetics, Jun. 20, 2016, vol. 17, No. 8, pp. 459-469.
Ester, M., et al., "A Density-Based Algorithm for Discovering Clusters a Density-Based Algorithm for Discovering Clusters in Large Spatial Databases with Noise," In Proceedings of the Second International Conference on Knowledge Discovery and Data Mining, KDD'96, Aug. 2, 1996, pp. 226-231, AAAI Press.
Graves, A., "Generating Sequences with Recurrent Neural Networks," Aug. 4, 2013, arXivpreprint arXiv:1308.0850.
Graves, A., et al., "Framewise Phoneme Classification with Bidirectional LSTM and Other Neural Network Architectures," Neural Networks, Jul.-Aug. 2005, vol. 18, No. 5, pp. 602-610.
International Search Report in corresponding/related International Application No. PCT/IB2018/058502, dated Mar. 18, 2019.
Ioffe, S., et al., "Batch Normalization: Accelerating Deep Network Training by Reducing Internal Covariate Shift," Feb. 11, 2015, arXiv:1502.03167.
Jain, C., et al., "A Fast Approximate Algorithm for Mapping Long Reads to Large Reference Databases," Research in Computational Molecular Biology, May 3-7, 2017, pp. 103812.
Jain, M., et al., "Nanopore Sequencing and Assembly of a Human Genome with Ultra-Long Reads," Nature Biotechnology, Apr. 2018, vol. 36, No. 4, pp. 338-345; additional Online Methods.
Kingma, D., et al., "Adam: A Method for Stochastic Optimization," Published as conference paper at ICLR 2015, Dec. 22, 2014, arXivpreprint arXiv:1412.6980, 15 pages.
Koren, S., et al., "Canu: Scalable and Accurate Long-Read Assembly Via Adaptive κ-mer Weighting and Repeat Separation," Genome Res, Mar. 15, 2017, vol. 27, No. 5, pp. 722-736.
Lee, H., et al., "Error Correction and Assembly Complexity of Single Molecule Sequencing Reads," BioRxiv, Jun. 18, 2014, 17 pages.
Li, H., "A Statistical Framework for SNP Calling, Mutation Discovery, Association Mapping and Population Genetical Parameter Estimation from Sequencing Data," Bioinformatics, Sep. 8, 2011, vol. 27, No. 21, pp. 2987-2993.
Li, H., "Minimap and Miniasm: Fast Mapping and de novo Assembly for Noisylong Sequences," Bioinformatics, Mar. 19, 2016, vol. 32, No. 14, pp. 2103-2110.
Li, H., "Minimap2: Fast Pairwise Alignment for Long Nucleotide Sequences," Bioinformatics, Sep. 15, 2018, vol. 34, No. 18, pp. 3094-3100.
Li, H., et al., "The Sequence Alignment/Map Format and SAMtools," Bioinformatics, Jun. 8, 2009, vol. 25, No. 16, pp. 2078-2079.
Li, Y., et al., "DeepSimulator: A Deep Simulator for Nanopore Sequencing," Bioinformatics, Apr. 6, 2018, vol. 34, No. 17, pp. 2899-2908.
Li, Y., et al., "DEEPre: Sequence-Based Enzyme EC Number Prediction by Deep Learning," Bioinformatics, Oct. 23, 2017, vol. 34, No. 5, pp. 760-769.
Loose, M., et al., "Real-Time Selective Sequencing Using Nanopore Technology," Nature Methods, Jul. 25, 2016, vol. 13, No. 9, pp. 751-754.
Lu, H., et al., "Oxford Nanopore MinION Sequencing and Genome Assembly," Genomics, Proteomics & Bioinformatics, Sep. 17, 2016, vol. 14, No. 5, pp. 265-279.
Maclean, D., et al., "Application of 'Next-Generation' Sequencing Technologies to Microbial Genetics," Nature Reviews Microbiology, Feb. 23, 2009, vol. 7, No. 4, pp. 287-296.
Metzker, M. L., "Sequencing Technologies—The Next Generation," Nature Reviews, Genetics, Jan. 2010, vol. 11, No. 1, pp. 31-46.
Ratkovic, M., Deep Learning Model for Base Calling of MinION Nanopore Reads, Master Thesis No. 1417, University of Zagreb, Faculty of Electrical Engineering and Computing, Jun. 1, 2017, pp. 1-48, Zagreb, Croatia.
Salvador, et al., "Toward Accurate Dynamic Time Warping in Linear Time and Space," Intelligent Data Analysis, Oct. 1, 2007, vol. 11, No. 5, pp. 561-580.
Simpson, J.T., et al., "Detecting DNA Cytosine Methylation using Nanopore Sequencing," Nature Methods, Apr. 2017, vol. 14, No. 4, pp. 407-410.
Sovic, I., et al., "Fast and Sensitive Mapping of Nanopore Sequencing Reads with Graphmap," Nature Communications, Apr. 15, 2016, vol. 7, 11307 (11 pages).
Stewart, J.B., et al., "The Dynamics of Mitochondrial DNA Heteroplasmy: Implications for Human Health and Disease," Nature Reviews Genetics, Sep. 2015, vol. 16, No. 9, pp. 530-542.
Stoiber, M., et al., "Basecrawller: Streaming Nanopore Basecalling Directly from Raw Signal," bioRxiv, May 1, 2017, 133058 (15 pages).
Swain, M.J., et al., "Color indexing," International Journal of Computer Vision, Jun. 6, 1991, vol. 7, No. 1, pp. 11-32.
Timp, W., et al., "DNA Base-Calling from a Nanopore Using a Viterbi Algorithm," Biophysical Journal, May 1, 2012, vol. 102, pp. L37-L39.

(56) References Cited

OTHER PUBLICATIONS

Trigeorgis, G., et al., "Deep Canonical Time Warping," In Proceedings of the 2016 IEEE Conference on Computer Vision and Pattern Recognition, 2016, pp. 5110-5118.

Vaser, R., et al., "Fast and Accurate de novo Genome Assembly from Long Uncorrected Reads," Genome Research, Jan. 18, 2017, 10 pages.

Written Opinion of the International Searching Authority in corresponding/related International Application No. PCT/IB2018/058502, dated Mar. 18, 2019.

Yang, C., et al., "NanoSim: Nanopore Sequence Read Simulator Based on Statistical Characterization." GigaScience, Feb. 21, 2017, vol. 6, No. 4, pp. 1-6.

Zeng, F., et al., "PyroHMMvar: A Sensitive and Accurate Method to Call Short Indels and SNPs for Ion Torrent and 454 Data," Bioinformatics, Aug. 31, 2013, vol. 29, No. 22, pp. 2859-2868.

\* cited by examiner

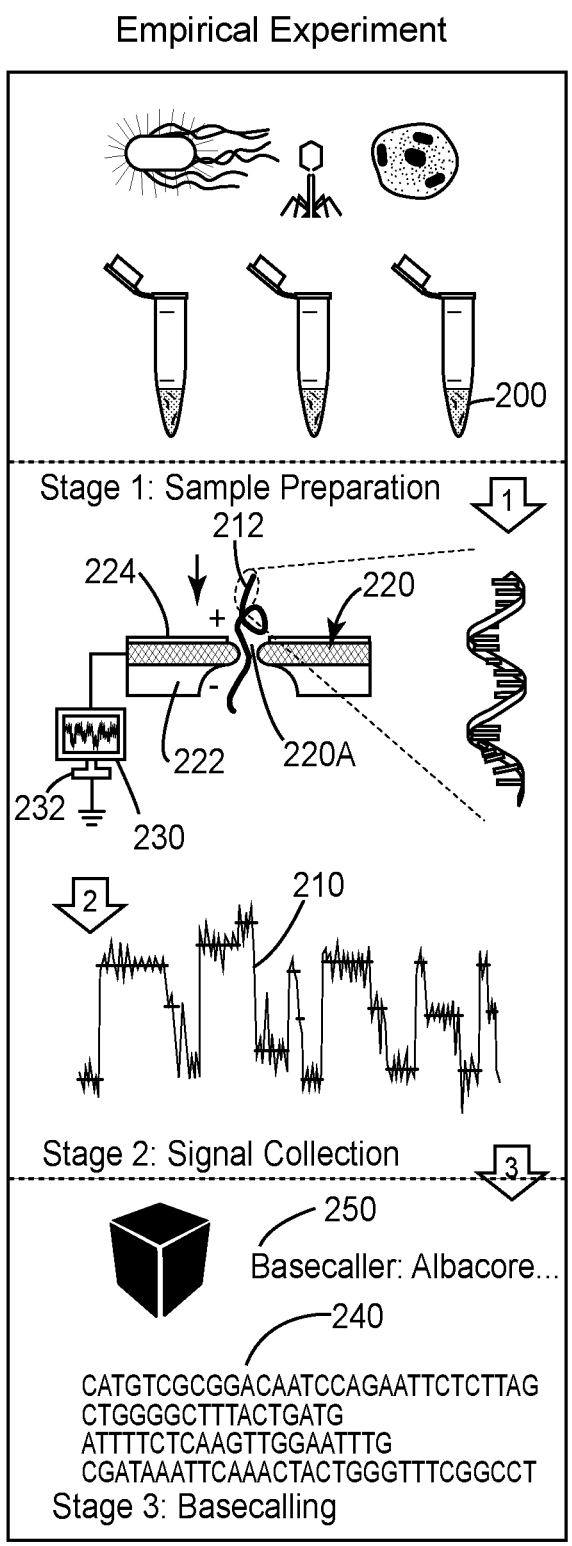
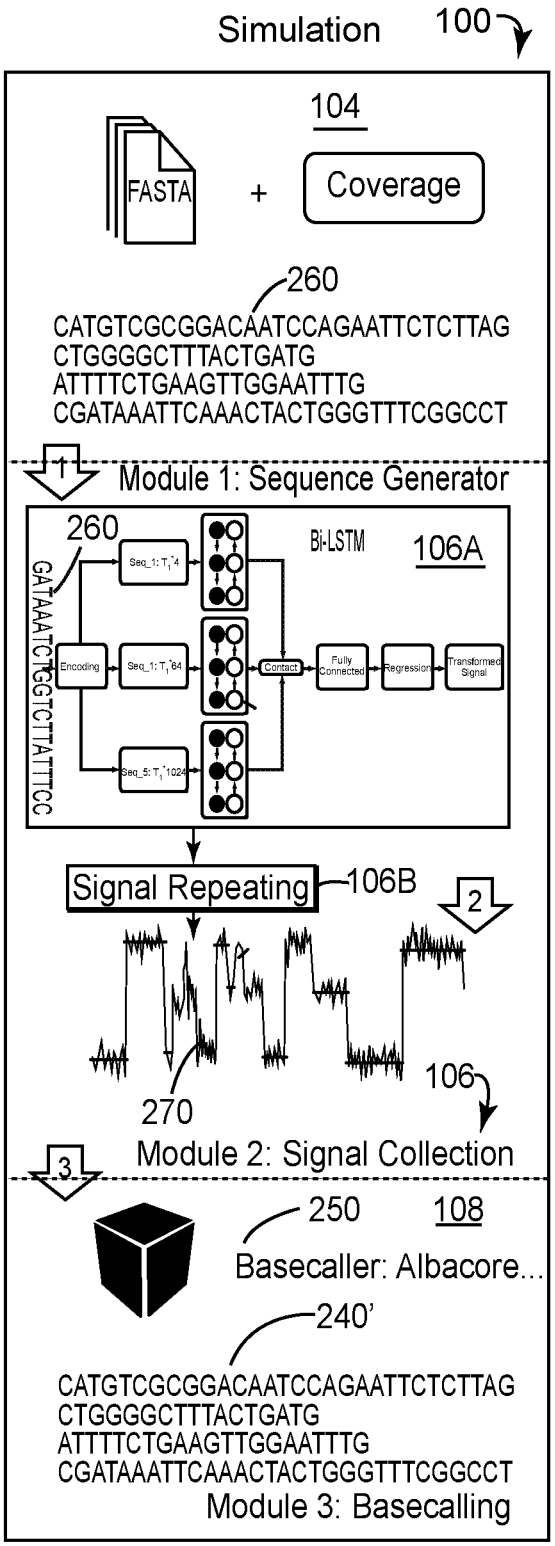

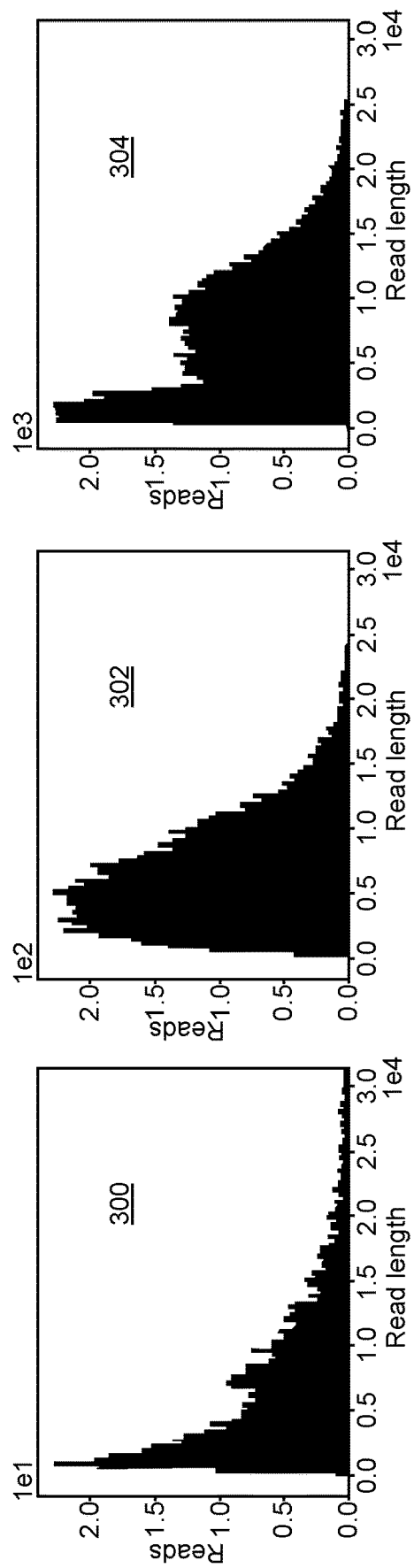

DEEPSIMULATOR METHOD AND SYSTEM FOR MIMICKING NANOPORE SEQUENCING

CROSS-REFERENCE TO RELATED APPLICATIONS

This application is a Continuation of U.S. patent application Ser. No. 16/769,127, filed on Jun. 2, 2020, which is a U.S. National Stage Application of International Application No. PCT/IB2018/058502, filed on Oct. 30, 2018, which claims priority to U.S. Provisional Patent Application No. 62/598,086, filed on Dec. 13, 2017, entitled "DEEPSIMULATOR: A DEEP SIMULATOR FOR MIMICKING NANOPORE SEQUENCING," U.S. Provisional Patent Application No. 62/599,908, filed on Dec. 18, 2017, entitled "DEEPSIMULATOR: A DEEP SIMULATOR FOR MIMICKING NANOPORE SEQUENCING," and U.S. Provisional Patent Application No. 62/702,161, filed on Jul. 23, 2018, entitled "DEEPSIMULATOR METHOD AND SYSTEM FOR MIMICKING NANOPORE SEQUENCING," the disclosures of which are incorporated herein by reference in their entirety.

BACKGROUND

Technical Field

Embodiments of the subject matter disclosed herein generally relate to a system and method for obtaining nucleotide sequence reads, and more specifically, mimicking all the stages of a Nanopore sequencing.

Discussion of the Background

Next-generation sequencing (NGS) technologies allow researchers to sequence DNA and RNA in a high-throughput manner, which have facilitated numerous breakthroughs in genomics, transcriptomics, and epigenomics (Metzker, 2010; MacLean et al., 2009). The most popular NGS technologies on the market include Illumina, PacBio, and Nanopore. Unlike the other sequencing technologies, Nanopore, whose core component is the pore chemistry that contains a voltage-biased membrane embedded with nanopores, detects electrical current signal changes when a DNA or RNA sequence is forced to pass through the pore by an applied voltage. Inputting the detected signals to a basecaller algorithm specifically designed for Nanopore, one can obtain the nucleotide sequence reads, as each sequence has its own "electrical signature." Benefited from the underlying design, Nanopore sequencing owns the advantages of long-reads (Byrne et al., 2017), point-of-care (Lu et al., 2016), and PCR-free (Simpson et al., 2017), which enable de novo genome or transcriptome assembling with repetitive regions, field real-time analysis, and direct epigenetic detection, respectively.

Along with the rapid development in Nanopore sequencing, down-stream data analytical methods and tools have also been explosively emerging. For example, Graphmap (Sovic et al., 2016), Minimap2 (Li, 2017) and MashMap2 (Jain et al., 2017a) were particularly designed to map the Nanopore data to the genome sequence. Canu (Koren et al., 2017) and Racon (Vaser et al., 2017) were created to assemble long and noisy reads produced by Nanopore. It is foreseeable that an even larger number of methods and tools would be developed in the near future for this method.

Therefore, it is desired to benchmark those new methods using either empirical data (i.e., experimentally obtained) or simulated data (Escalona et al., 2016). Although it is essential that one should run the method on the empirical data, the empirical data is sometimes difficult and expensive to obtain, with unknown ground truth. On the contrary, the simulated data can be easily obtained at a low cost, and its ground truth can be under full control. These features allow the simulated data to serve as the cornerstone to benchmark new methods.

Despite the existence of more than twenty simulators for NGS technologies, there are only three simulators created for the Nanopore sequencing, namely ReadSim (Lee et al., 2014), SiLiCO (Baker et al., 2016), and NanoSim (Yang et al., 2017). Although there are some differences between these three simulators, they share the same property of generating the simulated data utilizing the input nucleotide sequence and the explicit profiles based on a statistical model. Here the profiles refer to a set of parameters, such as insertion and deletion rates, substitution rates, read lengths, error rates and quality scores. For instance, ReadSim uses the fixed profile, SiLiCO uses the user provided profile, and NanoSim uses the user provided empirical data to learn the profile which would be used in the simulation stage.

However, these simulators do not truly capture the complex nature of the Nanopore sequencing procedure, which contains multiple stages including sample preparation, current signal collection, and basecalling. More importantly, the current signal is the essence of Nanopore sequencing and there is no simulator that attempts to mimic the signal generation step.

Thus, there is a need for a versatile Nanopore sequencing simulator to complement the experimentally obtained data as well as to benchmark those newly developed tools, as the currently available simulators are based on simple statistics of the produced reads, which is difficult to capture the complex nature of the Nanopore sequencing procedure, the main task of which is the generation of raw electrical current signals.

SUMMARY

According to an embodiment, there is a method for sequencing biopolymers, the method including selecting with a sequence generator module an input nucleotide sequence having plural k-mers; simulating with a deep learning simulator, actual electrical current signals corresponding to the input nucleotide sequence; identifying reads that correspond to the actual electrical current signals; and displaying the reads. The deep learning simulator includes a context-dependent deep learning model that takes into consideration a position of a k-mer of the plural k-mers on the input nucleotide sequence when calculating a corresponding actual electrical current.

According to another embodiment, there is a computing device for sequencing biopolymers, the computing device including a processor and a display. The processor is configured to select with a sequence generator module an input nucleotide sequence having plural k-mers, to simulate with a deep learning simulator, actual electrical current signals corresponding to the input nucleotide sequence, and to identify reads that correspond to the actual electrical current signals. The display is configured to display the reads. The deep learning simulator includes a context-dependent deep learning model that takes into consideration a position of a k-mer of the plural k-mers on the input nucleotide sequence when calculating a corresponding actual electrical current.

According to yet another embodiment, there is a non-transitory computer readable medium including computer executable instructions, wherein the instructions, when executed by a processor, implement instructions for sequencing biopolymers as discussed above.

BRIEF DESCRIPTION OF THE DRAWINGS

The accompanying drawings, which are incorporated in and constitute a part of the specification, illustrate one or more embodiments and, together with the description, explain these embodiments. In the drawings:

FIG. 2A illustrates an actual nucleotide Nanopore sequencer while FIG. 2B illustrates the DeepSimulator that mimics the Nanopore sequencer;

FIGS. 3A to 3C illustrate various distributions used to select a length of the reads;

DETAILED DESCRIPTION

The following description of the embodiments refers to the accompanying drawings. The same reference numbers in different drawings identify the same or similar elements. The following detailed description does not limit the invention. Instead, the scope of the invention is defined by the appended claims.

Reference throughout the specification to "one embodiment" or "an embodiment" means that a particular feature, structure or characteristic described in connection with an embodiment is included in at least one embodiment of the subject matter disclosed. Thus, the appearance of the phrases "in one embodiment" or "in an embodiment" in various places throughout the specification is not necessarily referring to the same embodiment. Further, the particular features, structures or characteristics may be combined in any suitable manner in one or more embodiments.

Figure 1:
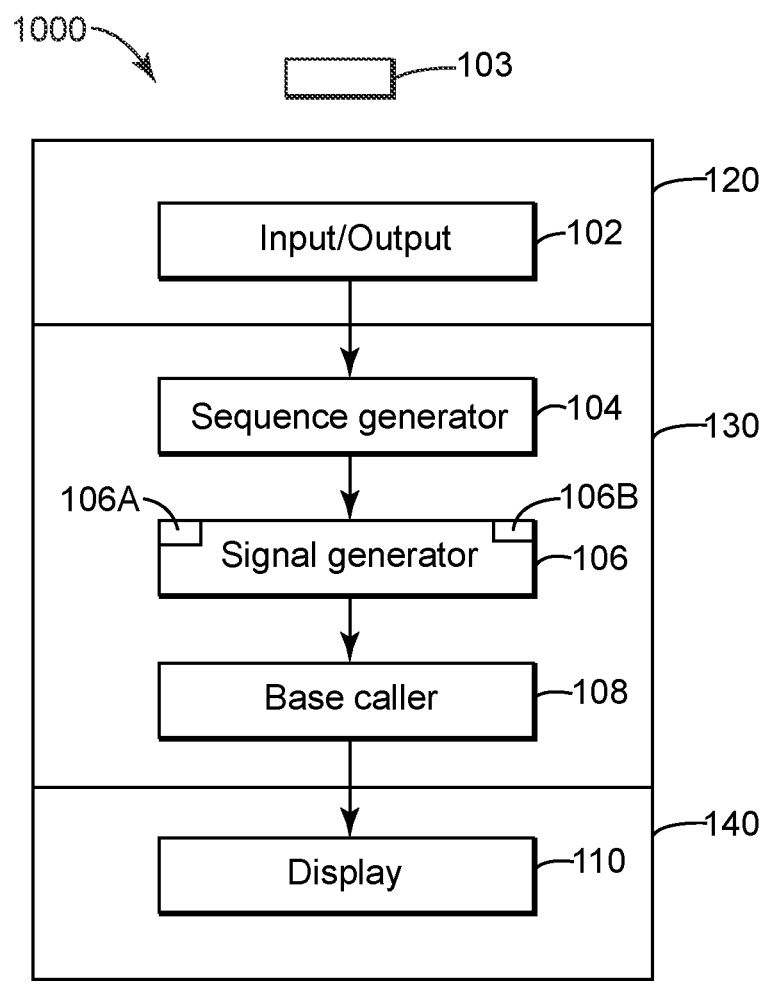
FIG. 1 is a schematic illustration of a DeepSimulator.

According to an embodiment, a novel Nanopore simulator 100, as illustrated in FIG. 1, requests from the user just to introduce at an input/output module 102, a reference genome or assembled contigs 103, specifying the coverage or the number of reads. The reference genome would then go through a sequence generator module 104 at a pre-processing stage, which produces several shorter sequences, satisfying the input coverage requirement and the read length distribution of the real Nanopore reads. Then, those sequences would pass through the signal generator module 106, which contains the pore model component 106A and the signal repeating component 106B. The pore model component 106A is used to model the expected current signal of a given k-mer (k usually equals 5 or 6 and here 5-mers are used without loss of generality), which is followed by the signal repeating component 106B, which produces the simulated current signals. These simulated signals are similar to the real signals in both strength and scale. Finally, the simulated signal would go through Albacore2, the official basecaller module 108, to produce the final simulated reads, which may be displayed on a display 110. The various components discussed herein may be implemented in a processor 130, the input/output module 102 may be implemented in dedicated circuitry 120, and the display 110 may be just one component of a results presenting system 140. For example, the system 140 may include a printer, or a drawing, or an electronic file.

Currently, the existing pore models (github.com/nanoporetech/kmer_models) are context-independent and they assign to each 5-mer a fixed value for the expected current signal, regardless of the location of the 5-mer on the nucleotide sequence. The novel pore model 106A is a context-dependent pore model, which takes advantage of a deep learning method, which has shown great potential in bioinformatics (see, for example, Alipanahi et al., 2015; Li et al., 2017; Dai et al., 2017). Nonetheless, as discussed later, it is challenging to train the deep learning model because of the fact that the current signal is usually 8-10 times longer than the nucleotide sequence. To solve this difficulty, a novel deep learning strategy BiLSTM-extended Deep Canonical Time Warping (BDCTW), which combines bi-directional long short-term memory (Bi-LSTM) (Graves and Schmidhuber, 2005) with deep canonical time warping (DCTW) (Trigeorgis et al., 2016) is used herein to solve the scale difference issue.

A pictorial representation of an empirical experiment associated with Nanopore and the simulation generated by the Deepsimulator are illustrated in FIGS. 2A and 2B. FIG. 2A shows the empirical experiment that is performed for determining the nucleotide sequence reads while FIG. 2B shows the simulation process of the DeepSimulator 100. The DeepSimulator 100 is "deep" in two folds. First, instead of being a simulator that only mimics the result, this simulator mimics the entire Nanopore sequencing. Secondly, when translating the initial sequence into the current signal, a context-dependent pore model is created using deep learning methods. By mimicking the way how the empirical Nanopore model works, the DeepSimulator simulates the complete Nanopore sequencing process, producing both the simulated current signals and the final reads. Also note that the DeepSimulator uses the basecaller module/software Albacore, which is also used by the Nanopore model. Employing the official basecaller, the DeepSimulator not only eliminates the procedure of learning the parameters in the profile, but also implicitly deploys the actual parameters. Furthermore, by dividing the simulation procedure into several modules, the DeepSimulator offers more flexibility. For instance, the user can choose to use a different basecaller, or tune the parameters in the signal generation module to obtain the final reads with different accuracies.

Thus, the DeepSimulator can fully simulate the entire procedure of the Nanopore sequencing, producing not only the final simulated reads, but also the intermediate electrical current signals. The DeepSimulator also uses a novel method to simultaneously handle the temporal alignment and the correlation analysis between the current signals and the DNA sequence that have large differences in the temporal scale. In doing so, the DeepSimulator is based on DCTW with Bi-LSTM as the feature mapping function for handling the sequential data. Also, in one embodiment, the DeepSimulator uses the first context-dependent pore model, which can accurately and specifically predict the expected current signal for each 5-mer of the DNA sequence, taking into account the sequentially contextual information.

The flow shown in FIG. 2A is now discussed in more detail. Unlike the previous simulators (Yang et al., 2017; Baker et al., 2016) that only simulate the final reads from statistical models, the DeepSimulator attempts to mimic the entire pipeline of the Nanopore sequencing. There are three main stages in the Nanopore sequencing shown in FIG. 2A. Each of these three stages is mimicked by the DeepSimulator illustrated in FIG. 2B. The first stage is sample preparation, which would result in the nucleotide specimen 200 used in the experiment. After obtaining the specimen 200, the next stage is to measure the electrical current signals 210 of the nucleotide sequences 212 that form the specimen 200, using a Nanopore sequencing device, such as Minion. The Nanopore sequencing device includes, at a minimum, a nanopore membrane 220 that is supported on a support 222. The membrane 220 may be protected with a protection layer 224. A power source 230 applies a voltage to the membrane 220, which makes the nucleotide sequences 212 to move through the pore 220A of the membrane 220. Each k-mer of the nucleotide sequences 212 changes the electrical properties of the nanopore, which makes a current recording device 232 to measure various current signals 210 corresponding to the various k-mers. These collected signals are usually stored in a FAST5 file. Finally, the reads 240' corresponding to the k-mers are obtained by applying a basecaller module 250 to the current signals 210, as illustrated in FIG. 2A.

In a similar manner, the DeepSimulator 100 has three modules, as illustrated in FIG. 2B. The first module 104 is the sequence generator. Providing the whole genome or the assembled contigs, as well as the desired coverage requirement, the DeepSimulator 100 generates the relatively shorter sequences 260, which satisfy the coverage requirement and the length distribution of the Nanopore reads. Details of the read length distribution are discussed later. Then, those generated sequences 260 are fed into the second module 106, namely the signal generator module. As the core module of the DeepSimulator, it is used to generate the simulated current signals 270 which aim to approximate the actual current signals measured by Minion in FIG. 2A. There are two components within this module: the pore model component 106A and the signal simulation component 106B. The pore model component 106A takes as input the nucleotide sequence 260 and outputs the context-dependent expected current signal for each 5-mer in the sequence 260, which is discussed in detail later. The signal simulation component 106B repeats the expected signal (which is output by the pore model component 106A) several times, at each position, based on a signal repeat time distribution and then adds a random noise to produce the simulated current signals 270. This component is also discussed later. The last module of DeepSimulator is the commonly used basecallers 250, similar to the Nanopore system illustrated in FIG. 2A.

Notice that during the entire simulating process in FIG. 2B, the DeepSimulator does not explicitly introduces mismatches and indels (insertions and deletions), which is usually performed by the existing statistical simulators (Yang et al., 2017; Baker et al., 2016) directly at the read-level. Instead, the DeepSimulator mimics the current signal 210 produced by the Nanopore sequencing of FIG. 2A, as similar as possible, making the basecaller 250 introduce mismatch and indel by itself. Thus, the mismatches and indels in the method used by the DeepSimulator are implicitly introduced at the signal-level, which is more reasonable and closer to the realistic situation. Details about the first and second modules 104 and 106 and their functionalities are now discussed.

The sequence generator module 104 of the DeepSimulator 100 needs to model the user-specified reference genome or assembled contigs, as well as the desired coverage or the number of reads. Thus, the sequence generation module 104 randomly chooses a starting position on the genome or contigs to produce the relatively shorter sequences 260, which satisfy the coverage requirement and the length distribution of the experimental Nanopore reads.

However, the read length of the actual Nanopore sequencing is not straightforward to model. Many factors, such as the experimental purpose and the experimenter's experience, would greatly influence the read length distribution. Thus, the present inventors have investigating the dataset published by Nanoporetech and data-sets provided by others, and found that the distribution of the read length can be categorized into three patterns, by using DBSCAN (Ester et al., 1996) as the clustering method and histogram intersection (Swain and Ballard, 1991) as the distance metric. FIGS. 3A to 3C show these three patterns. For the first pattern 300 shown in FIG. 3A, an exponential distribution is used to fit the reads for the human genome. For the second pattern 302 shown in FIG. 3B, a beta distribution is used to fit the reads for the E. coli genome. For the last pattern 304 shown in FIG. 3C, it cannot be fit using a single distribution (e.g., reads for lambda phage genome). Thus, in one application, a mixture distribution of two gamma distributions is used to describe pattern 304. When using the DeepSimulator, the users can choose either of the three patterns. Alternatively, the user can also specify other distribution patterns for the read length.

Next, the context-dependent pore model 106A is discussed. Given a nucleotide sequence 260 as shown in FIG. 2B, the first step is to simulate its corresponding current signal 270. The current signal 270 is affected by the advance of the nucleotide sequence via the pore model 106. In this embodiment, it is first formulated the problem of building the pore model, followed by the corresponding solution BiLSTM-extended Deep Canonical Time Warping (BDCTW). The BDCTW algorithm is divided into three parts: (1) general framework of deep canonical time warping, (2) feature representation, and (3) neural network architecture. Then, the context-dependent pore model is generated.

With regard to formulating the problem of building the core model, according to an embodiment, the pore model is defined as the correspondence between the expected current signal and the 5-mer nucleotide sequence that is in the pore at the same time (see, for example, Deamer et al., 2016). The pore model prediction problem is formulated as follows: given as input a nucleotide sequence $X=x_1, x_2, \ldots, x_{T_1}$ with $T_1$ nucleotides where $x_i$ is a 4-state nucleotide base that can take one of the four values from the set $\{A,T,C,G\}$ for DNA or from the set $\{A,U,C,G\}$ for RNA, the pore model 106A needs to mathematically predict the corresponding expected electrical current signals $Y=y_1, y_2, \ldots, y_{T_1-4}$, where $y_i$ is the predicted expected electrical current signal of a 5-mer starting from position i in the nucleotide sequence X (e.g., "ACGTT").

According to an embodiment, a novel method for building the pore model in consideration of the contextual information is now discussed. Specifically, this novel method learns the context-dependent (or position-specific) pore model $Y^{dep}$ with length T1-4 for the nucleotide sequence X with length T1 from the raw signals 210 (i.e., the observed current signals from a Nanopore sequencing device as illustrated in FIG. 2A). The raw signals 210 are considered herein to be mathematically described by a sequence $\hat{Y}$ having a length T2.

There are three challenges for learning the context-dependent pore model. A first challenge is the scale difference. Because the frequency of the original electrical current measurements (taken at 4000 Hz) 210 is about 8-10 times faster than the speed at which the single-strand nucleotide sequence passes through the pore (the translocation speed is around 450 bases per second) (Stoiber and Brown, 2017), the temporal scale difference between the raw signals $\hat{Y}$ and the nucleotide sequence X is large.

A second challenge is the dimensionality difference. The feature space dimensionality is different between X and $\hat{Y}$, due to the fact that $\hat{Y}$ is a one-dimensional electrical current signal sequence whereas X is a nucleotide sequence with the feature dimension being at least four. This is so because in order to preserve the original sequence information, one-hot encoding is commonly used (Graves, 2013) and thus four-dimension is needed to encode the four nucleotide bases. A basic definition of the one-hot encoding is a group of bits among which the possible combinations of values are only those with a single high (1) bit and all the others are low (0) bits.

A third challenge is the complex non-linear correlation of these sequences. The measurement of the raw signals $\hat{Y}$ takes place under an extremely noisy environment because of voltage changes, noise, interactions between nanopore channels, etc. (David et al., 2016). Thus, the relationship between X and $\hat{Y}$ is very complex, having high-order or non-linear correlation.

Figure 4:
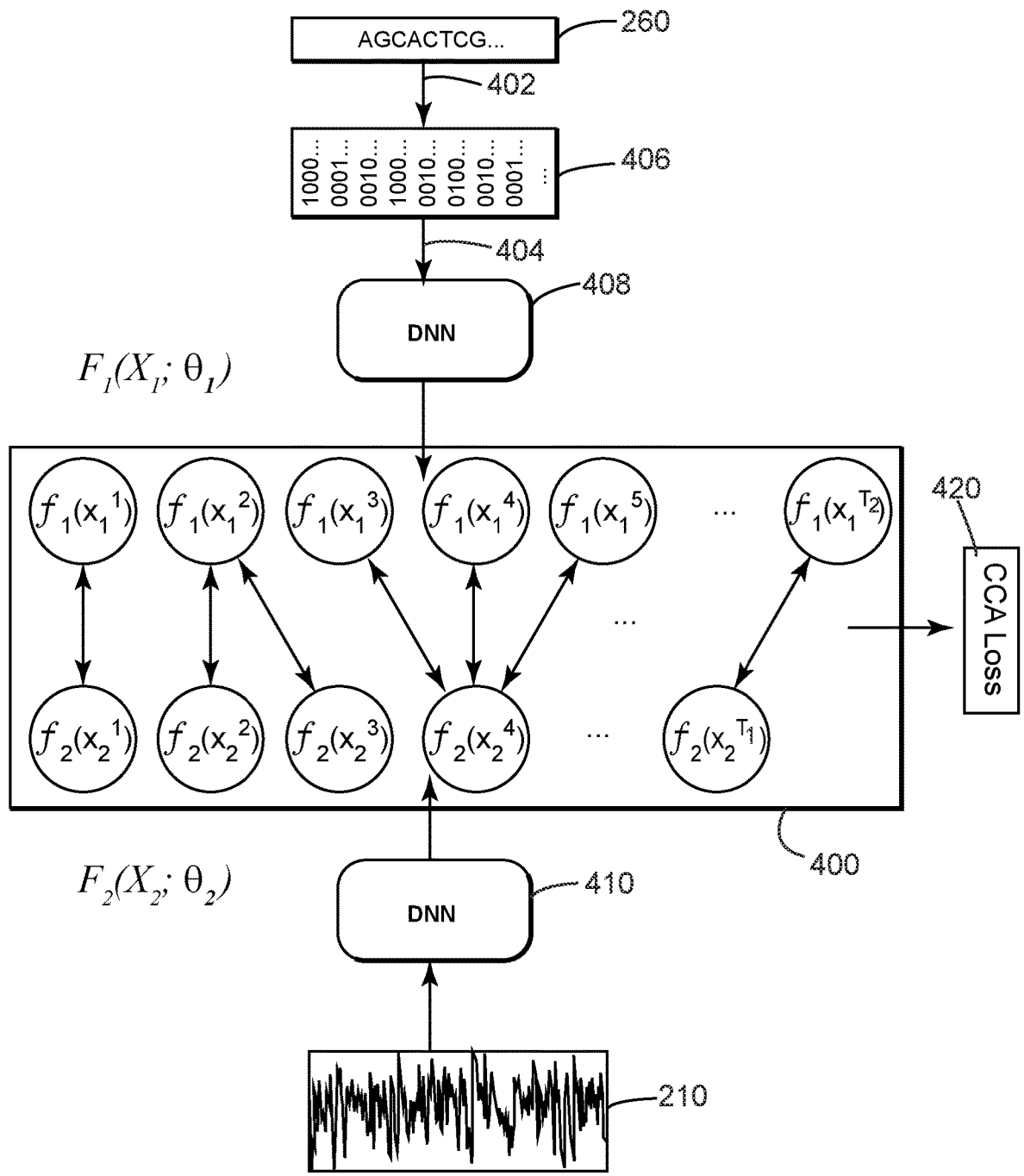
FIG. 4 illustrates how two different sets of data are transformed to a common space with a deep learning neural network algorithm.

According to a first part (1) of the BDCTW algorithm, a general framework of a deep canonical time warping is now introduced. The goal of the deep canonical time warping (DCTW) algorithm is to discover a hierarchical or recurrent non-linear relationship between two input linearly structured data sets $X_1$ and $X_2$ with different lengths $L_1$, $L_2$ and feature dimensionality $d_1$, $d_2$ (i.e., $X_i \in \mathbb{R}^{d_i \times L_i}$) (Trigeorgis et al., 2016). That is, DCTW simultaneously performs spatial transformation and temporal alignment between the two input data sequences. In this case, the two inputs are the nucleotide sequence X (element 260 in FIG. 2B) and the observed electrical current signal sequence $\hat{Y}$ (element 210 in FIG. 2A). The goal of this step is to transform the two sequences into a common space 400, as shown in FIG. 4 so that the elements of the nucleotide sequence X are associated with real measurements from the current signal sequence $\hat{Y}$. Thus, each of the two sequences X and $\hat{Y}$ need to be transformed. The sequence X is first encoded in step 402 by being, for example, digitized. Then, in step 404, the encoded sequence 406 is fed to a deep neural network (DNN) algorithm 408 to perform a spatial transformation. The DNN 408 is used to learn from known data (i.e., raw signal 210). The raw data 210 is also fed to a DNN to perform a spatial transformation. Note that the raw data 210 is actual data and thus, only the sequence 260 needs to be fit to the raw data.

After the DCTW illustrated in FIG. 4, the transformed features $f_1$ and $f_2$ for X and $\hat{Y}$, respectively, are not only temporally aligned with each other, but also maximally correlated. To this end, consider that $Y_i = F_i(X_i; \theta_i)$ represents the activation function of the final layer of the corresponding DNN for Xi, which has d maximally correlated units, where $d \leq \min(d1, d2)$. Note that $F_1$ in FIG. 4 corresponds to the sequence 260 and $F_2$ corresponds to the raw signal 210. Such an operation reduces the input data samples to the same feature dimension and then performs a maximal correlation analysis, which essentially resembles the classical canonical correlation analysis (CCA) (Akaike, 1976).

Consequently, this embodiment optimizes the following objective function 420:

$$\operatorname{argmin}_{\theta_1, \theta_2, \Delta_1, \Delta_2} \|F_1(X_1; \theta_1)\Delta_1 - F_2(X_2; \theta_2)\Delta_2\|_F^2$$

subject to: $F_i(X_i; \theta_i)\Delta_i 1_T = 0_d$, $F_i(X_i; \theta_i)\Delta_i \Delta_i^T F_i(X_i; \theta_i)^T = I_d$, $F_1(X_1; \theta_1)\Delta_1 \Delta_2^T F_2(X_2; \theta_2)^T = D_d$, $\Delta_i \in \{0,1\}^{T_i \times T}, i = \{1,2\}$, (1)

where $X_1 = X$ and $X_2 = \hat{Y}$. $T_1$, $T_2$ and T are the lengths of X, $\hat{Y}$, and the final alignment, respectively. $\Delta_i$ are the binary selection matrices that encode the alignment paths for $X_i$. That is, $\Delta_1$ and $\Delta_2$ remap the nucleotide sequence X with length $T_1$ and raw signals $\hat{Y}$ with length $T_2$ to a common temporal scale T in space 400. D is a diagonal matrix and I is the identity matrix. Vector 1 (0) is an appropriate dimensionality vector of all 1's (0's).

Such an objective function can be solved via alternating optimization (Trigeorgis et al., 2016). Specifically, given the final layer output $F_i(X_i; \theta_i)$, the method employs dynamic time warping (DTW) (Salvador and Chan, 2007) to obtain the optimal warping matrices $\Delta_i$, which temporally align the input sequence $X_i$ and the final alignment. After obtaining the warping matrices $\Delta_i$ via DTW, the maximally correlated nonlinear transformation is inferred on the temporally aligned input features $F_i(X_i; \theta_i)$ by maximizing the following function:

$$\operatorname{corr}(F_1(X_1; \theta_1)\Delta_1, F_2(X_2; \theta_2)\Delta_2) = \|K_{DCTW}\|_*, \quad (2)$$

where $\|\cdot\|_*$ is the nuclear norm, $K_{DCTW} = \hat{\Sigma}_{11}^{-1/2} \hat{\Sigma}_{12} \hat{\Sigma}_{22}^{-1/2}$ is the kernel matrix of DCTW, $$\hat{\Sigma}_{ij} = \frac{1}{T-1} F_i(X_i; \theta_i)\Delta_i C_T \Delta_j^T F_j(X_j; \theta_j)^T$$

denotes the empirical covariance between the transformed data sets, where $C_T$ is the centering matrix, $$C_T = I - \frac{1}{T} 11^T.$$

The gradient of the objective function $\|K_{DCTW}\|_*$ with respect to the activation layer of one neural network, such as $Y_1 = F_1(X_1; \theta_1)$, can be calculated as:

$$\partial \|K_{DCTW}\|_* = \frac{1}{T-1}(F^{(pos)} - F^{(neg)}), \quad (3)$$

$$F^{(pos)} = \hat{\Sigma}_{11}^{-1/2} UV^T \hat{\Sigma}_{22}^{-1/2} Y_2 \Delta_2 C_T, \text{ and}$$

$$F^{(neg)} = \hat{\Sigma}_{11}^{-1/2} USU^T \hat{\Sigma}_{11}^{-1/2} Y_1 \Delta_1 C_T,$$

where $USV^T = K_{DCTW}$ is the singular value decomposition (SVD) of the kernel matrix $K_{DCTW}$. By employing this equation as the sub-gradient, it is possible to optimize the parameters $\theta_i$ in each neural network DNN via back-propagation.

Because the electrical current signal of a 5-mer could be influenced by the surrounding sequences, in this embodiment, the feature function $F_1(X_1; \theta_1)$ is extended in the original DCTW with bi-directional long short-term memory (Bi-LSTM) (Boza et al., 2017) to incorporate the contextual information. The DNN architecture in FIG. 4 is further discussed with reference to FIG. 5. Note that in FIG. 4, elements $f_1(x_1)$ correspond to the activation function $F_1$ of the final layer of DNN 408 and elements $f_2(x_2)$ correspond to the activation function $F_2$ of the final layer of DNN 410. In one embodiment, only the DNN 408 is used for the learning process as the raw signal 210 does not need to learn anything, i.e., only the sequence 260 is learning which electrical signals from the raw signals 210 correspond to each of its elements.

According to a second part (2) of the BDCTW algorithm, the feature representation is now discussed. To preserve the original sequence information, this embodiment uses a one-hot encoding for the representation of the nucleotide sequence X. When a nucleotide sequence passes through the nanopore, each 5-mer inside the pore will cause a change in the magnitude of the electrical current. Thus, instead of just considering one nucleotide ($4^1=4$ combinations) at position t, this embodiment also encodes the 3-mer ($4^3=64$ combinations) and the 5-mer ($4^5=1024$ combinations) centered at position t as well.

Figure 5:
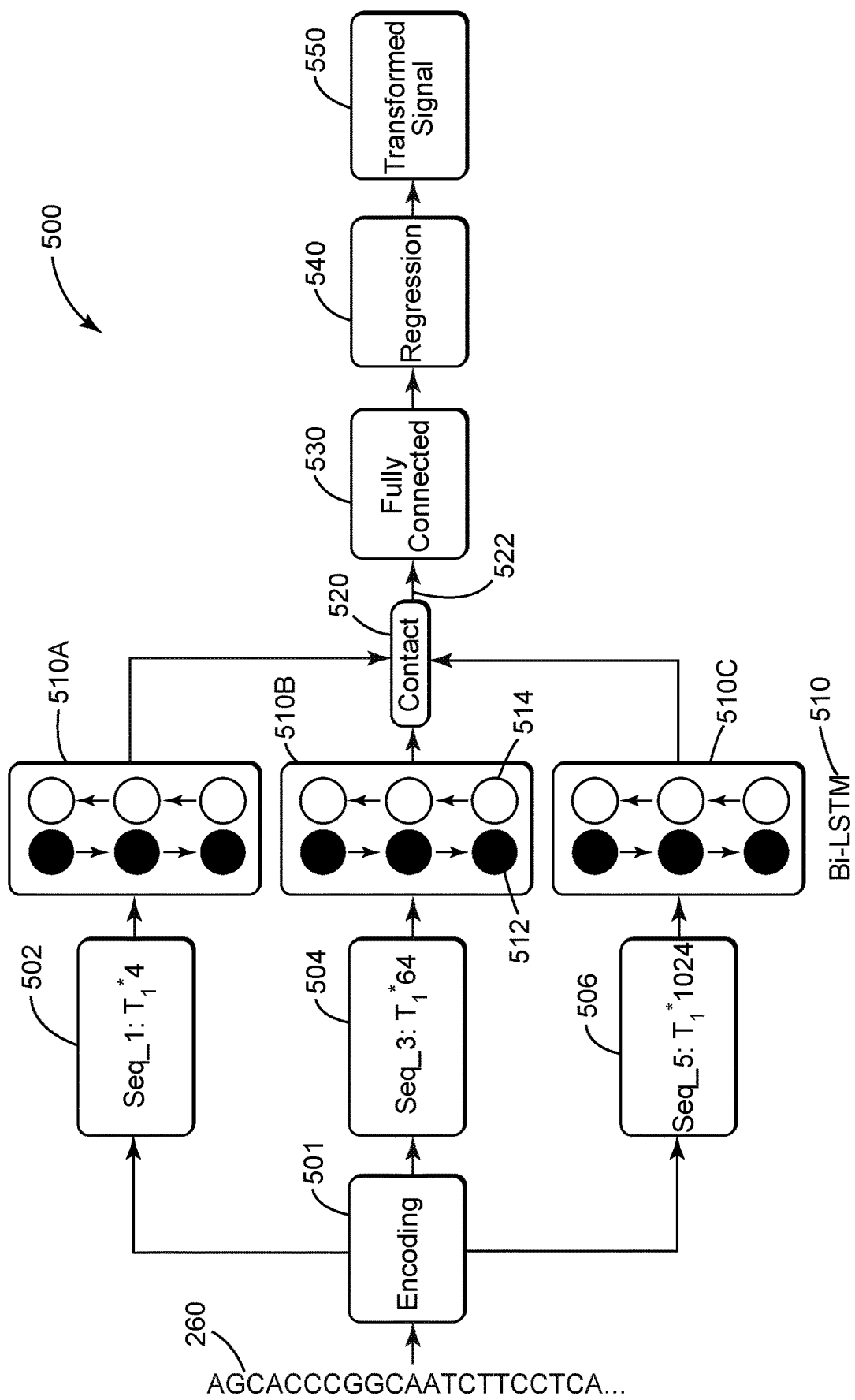
FIG. 5 illustrates the structure of a context-dependent pore model component.

Specifically, this embodiment uses one "1" and $4^k-1$ "0"s (necessary for the one-hot encoding) to represent each k-mer ($k \in \{1, 3, 5\}$). Then, for each nucleotide sequence X 260 with a length T1, as shown in FIG. 5, the one-hot encoding 501 would produce three feature matrices 502, 504, 506, with dimensions T1×4, T1×64, and T1×1024, respectively. Each row in a feature matrix 502 or 504 or 506 represents a specific position and each column represents the appearance of a certain k-mer.

According to a third part (3) of the BDCTW algorithm, the neural network architecture 500 is discussed with regard to FIG. 5. To simplify the model architecture 500, an identical transformation is used as the feature mapping (for DNN 410 in FIG. 4) to deal with the raw signal data 210. That is, this embodiment sets $F_2(X_2; \theta_2)=\hat{Y}$. For the other feature mapping function $F_1(X_1; \theta_1)$ for the nucleotide sequence 260 (see FIG. 4), the Bi-LSTM architecture 510 is used. Specifically, as shown in FIG. 5, for each feature matrix 502, 504, and 506, this embodiment uses a Bi-LSTM block 510A, 510B, and 510C, respectively, to obtain the hidden representation, with 50 forward LSTM cells 512 and 50 backward LSTM cells 514.

After concatenating in step 520 the hidden representations of the feature matrices, the method feeds the concatenated representation 522 into a fully-connected layer 530 with 200 nodes, which is followed by a regression layer 540, after which a transformed signal 550 is generated. All the weights are initialized using the Xavier method. To avoid overfitting, this embodiment utilizes weight decay with the coefficient as $1e^{-4}$. In one application, it is possible to choose Adam (Kingma and Ba, 2014) as the optimizer with the learning rate $1e^{-4}$. Deploying batch normalization (Ioffe and Szegedy, 2015) to accelerate the train, the batch size is set as 64 during training. The deep neural network model 500 is implemented using Tensor-flow (Abadi, 2016) and can converge within 6 hours with the help of two Pascal Titan X cards, which is faster than the existing simulators.

The deep neural network 500 in deep canonical time warping for feature mapping of the input nucleotide sequence 260 shown in FIG. 5 becomes the context-dependent pore model 106A after training. To use it, the pore model 106A first uses a one-hot vector encoding of k-mers, where k=1, 3, 5, to encode the input sequence 260. The encodings then go through BiLSTM layers 510, fully-connected layers 530 as well as the final regression layer 540 to generate the expected electrical signals 550.

After obtaining the expected current signals 550 of a given nucleotide sequence 260, the next simulation step performed by the signal generator module 106 is to repeat the expected electrical signals 550 at each position and add random noise. As previously discussed, this is achieved by the signal repeating component 106B. It is well-known that during sequencing, the raw signal 210's acquisition speed is much faster than the DNA or RNA moving speed, causing a certain 5-mer being measured multiple times. Thus, to convert the expected signals 550 produced by the pore model 106A, to the current signals 270, which can be put into the basecaller model 250, it is necessary to repeat a certain expected signal 550 several times. Similar to the read length method discussed with regard to FIGS. 3A to 3C, in this embodiment, the repeat time is modeled using a mixture of alpha distributions. When running the DeepSimulator, the repeat time would be drawn from the distribution for each position on the expected signal, generating the simulated current signal by repeating that position for a certain number of times. It should also be noted that the raw signals are extremely noisy due to the complicated sequencing environment, including voltage changes, noise and interactions between channels (David et al., 2016). Therefore, in one application, Gaussian noise is added with the user-defined variance parameter to each position of the simulated signals.

Figure 6:
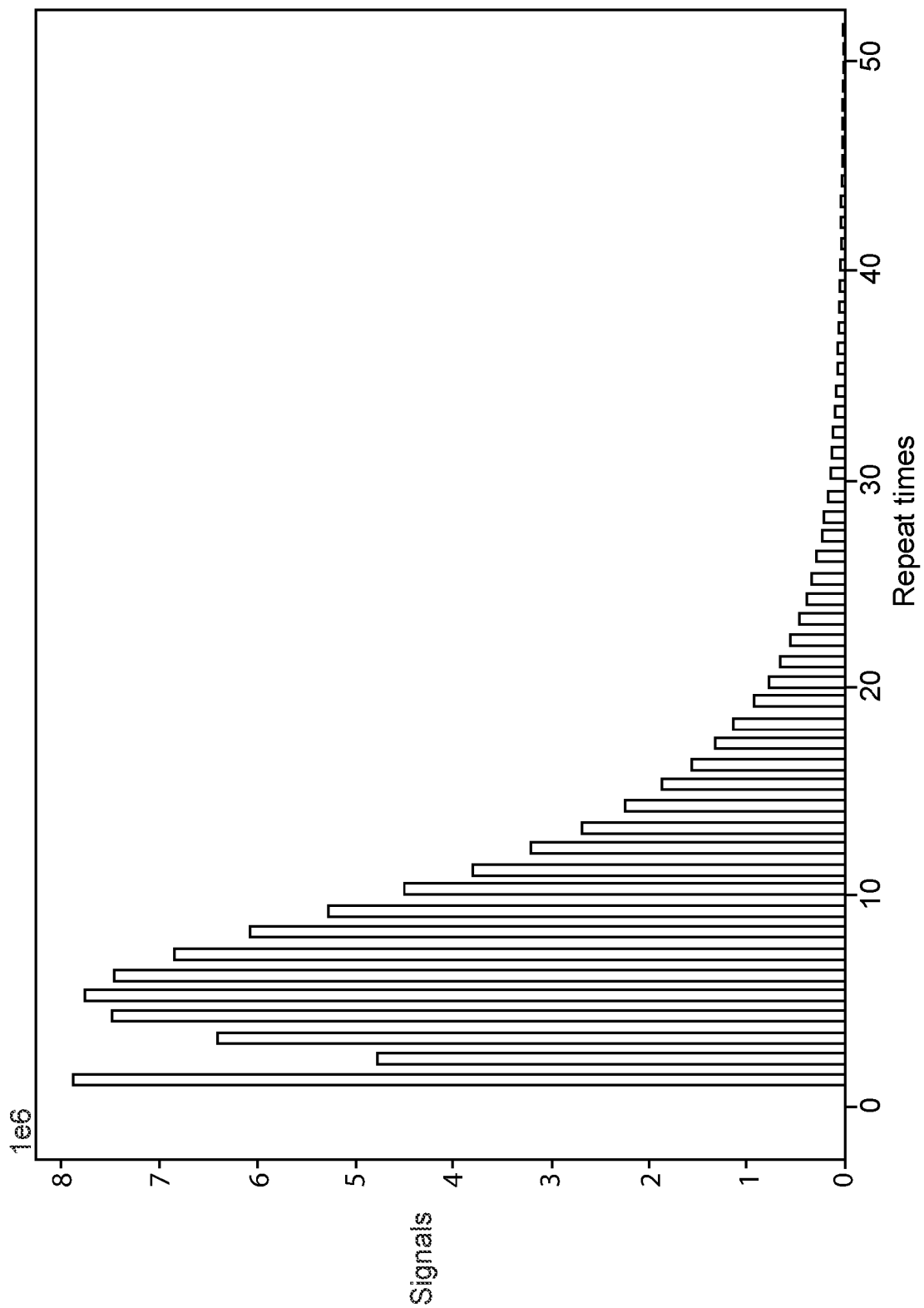
FIG. 6 illustrates a distribution used by a signal repeating component to repeat a signal generated by the context-dependent pore model.

One difficulty of this step is to get the statistics of the repeat time, as shown in FIG. 6. Currently, it is almost impossible to get the precise repeat time of a certain 5-mer, but it is possible to obtain the approximate repeat time statistics. Thus, in this embodiment, four steps are used for obtaining the statistics. In the first step (i), take as input the reference genome 260, raw signals 210 produced by Minion, and the basecalled reads 240 from Albacore and map the reads onto the reference genome by Minimap (Li, 2016), which would mark out the ground truth (at least approximate) sequence that corresponds to the raw signal. In the second step (ii), with the ground truth sequence, get the expected signal of each 5-mer in the sequence using the context-dependent pore model 106A. In the third step (iii), apply dynamic time warping (DTW) (Salvador and Chan, 2007) to map the raw signal 210 and the expected signal 550, which is based on the fact that those two signals should have the similar shape. In the fourth step (iv), based on the mapping, it is possible to find out the repeat time from the raw signal positions that correspond to each expected signal position. Performing the above method on a large dataset, it is possible to obtain a stable statistic of the repeat time. Then, the method fits the distribution as a mixture model.

To test the DeepSimulator 100 introduced above, four Nanopore sequencing datasets from different species were used, ranging from three in-house datasets: lambda phage, *E. coli* K-12 sub-strain MG1655, and *Pandoraea pnomenusa* strain 6399, to the publicly available human data. In particular, all the samples were sequenced on the MinION device with 1D protocol on R9.4 flow cells (FLO-MIN106 protocol). The publicly available human dataset is the human chromosome 21 from the Nanopore WGS Consortium (Jain et al., 2017b). The samples in this dataset were sequenced from the NA12878 human genome reference on the Oxford Nanopore MinION using 1D ligation kits (450 bp/s) with R9.4 flow cells. The Nanopore raw signal datasets in the FAST5 format were downloaded from nanopore-wgs-consortium4. The reference genomes of the four datasets were downloaded from NCBI5.

The context-dependent pore model 106A of the second module 106 in the DeepSimulator 100 was trained on the *Pandoraea pnomenusa* dataset. To construct a dataset that is discussed later, which is used to check the performance of the pore models, 700 reads were randomly sampled from each of remaining three species to form a dataset containing 2100 reads.

In addition to the four species for which there are both the reference genome and the empirical experimental data, another extremely small genome was included, mitochondria, for which there is only the reference genome. The *E. coli* K-12 genome, the lambda phage genome, and the mitochondrial genome were used to perform the assembly experiments to be discussed next. Finally, the mitochondrial genome and lambda phage genome were used for the SNP calling experiments.

The inventors have evaluated each of the three modules 104, 106 and 108 of the DeepSimulator 100 and the results show that (i) the length distribution of the simulated reads satisfies the empirical read length distribution; (ii) the signals generated by the context-dependent pore model are more similar to the experimental signals than the signals generated by the official context-independent pore model; and (iii) the final reads generated by the Deepsimulator with the default parameter have almost the same profile as the experimental data.

For an input genome sequence, the DeepSimulator generates reads whose length distribution satisfies the empirical length distribution. Three predefined distributions were provided: the beta distribution (see FIG. 3A), the exponential distribution (see FIG. 3B), and the mixed gamma distribution (see FIG. 3C), which cover the three main patterns of the Naonpore read length distribution. In general, the mixed gamma distribution is often the most suitable length distribution. As a result, this last distribution was selected as the default length distribution pattern. In addition to that, considering the property of different sequencing tasks, some biological experiments may be designed on purpose so that the read length distribution would satisfy a predefined distribution. In order to mimic that case, the sequence generator module 104 also provides an interface so that the user can enter a user-defined read length distribution. The distributions of the length of the simulated reals by DeepSimulator on human, *E. coli* K-12 sub-strain MG1655, and lambda phage were found to be very similar to that of the experimental reads.

To check the signal-level similarity between the simulated signals 270 generated by the DeepSimulator 100 and the experimental ones 210 produced by Minion (i.e., the raw signals), a dynamic time warping (DTW) (Salvador and Chan, 2007) was employed, which is the standard way of checking the difference between two signal sequences on the randomly selected 2100 reads from lambda phage, *E. coli* K-12 sub-strain MG1655, and human. The average deviation between them is 0.175. The same analysis was also performed using the official content-independent pore model followed by the same signal repeat component used in the DeepSimulator to obtain the context-independent simulated signals. Using the same set of reads, the average deviation of the context-independent signals from the raw signals is 0.185, which is about 5.7% higher than that of the DeepSimulator.

Furthermore, another experiment was performed on the reads generated by NanoSim (Yang et al., 2017) to derive the simulated signals by their context-independent pore model.

The average deviation of the NanoSim signals to the raw ones is 0.210, which is 20% higher than that of the DeepSimulator.

For the read-level outputs, a parameter interface is provided in the DeepSimulator 100, which can be adjusted continuously so that the user could control the final read basecalling accuracy as well as the indel ratio. Internally, the parameters change the noise and the signal repeat time distribution, which are the two factors that affect the read profile greatly. To check the read profile of the simulated reads, for a given input ground truth sequence, the DeepSimulator was run to obtain the simulated read. Performing BLAST (Altschul et al., 1997) between the simulated read and the input ground truth read, it was possible to calculate the profiles such as the accuracy, mismatch number, and gap numbers. According to this experiment, the output reads of the DeepSimulator can have a basecalling accuracy ranging from 83% to 97%. In this regard, the basecalling module is configured to assign a base to an actual electric current. Thus, when the actual electrical current signals 270 in FIG. 2B are supplied to the basecaller module 250, the basecaller module outputs the reads 240', which include the plural bases of the selected nucleotide sequence 260 that was originally input to the DeepSimulator.

Because of the long reads, Nanopore sequencing has higher potential in genome assembly than the other sequencing technologies. Thus, one of the main applications for Nanopore sequencing is de novo assembly. Two wide-recognized de novo assembly pipelines, Canu (Koren et al., 2017) and Miniasm (Li, 2016) with Racon (Vaser et al., 2017), were used to perform such task on two different sets of simulated reads generated by the DeepSimulator from the *E. coli* K-12 genome and the lambda phage genome, respectively. Both of the two experiments succeeded in assembling the simulated reads into one contig. The comparison between the assemblies and the reference genome was plotted using MUMmer (Delcher et al., 1999). A comparison of these assemblies with the assembly results of *E. coli* K-12 and lambda phage using the empirical data illustrate that the results of the empirical data show similar patterns as the results of the simulated data. In addition to the relatively large genome, *E. coli* K-12, which is 4.6 Mbp, and a small genome, lambda phage, which is 48 Kbp, another experiment was performed on an extremely small genome, the mitochondrial genome (16 Kbp). Miniasm with Racon also succeeded in assembling the simulated reads into one contig.

Single nucleotide polymorphisms (SNPs) are found to be involved in the etiology of many human diseases. For example, hundreds of SNPs in the mitochondiral DNA (mtDNA) have been linked to aging-related genes (Stewart and Chinnery, 2015). Despite the importance of the complete haplotyping of the mitochondrial genome, the current methods, which are designed for detecting mitochondrial mutations from a population of cells, would perform massively parallel sequencing of short DNA fragments, having difficulty in performing the complete haplotyping.

On the other hand, the Nanopore sequencing, which has the potential of performing the long-read single-molecular sequencing of mtDNA, may overcome the hurdle. Under that circumstance, mimicking the ideal single molecular Nanopore sequencing scenarios, experiments were conducted on the success rate of SNPs detection with respect to the sequencing coverage, using the simulated reads from the DeepSimulator. Note that a long-read sequencing is considered to have average fragment lengths of over 10,000 base-pairs.

Considering the low basecalling accuracy of the Nanopore sequencing, although the current basecalling accuracy is not high enough (around 86% to 88%), theoretically, it is possible to consider those errors as random errors instead of systematic errors, and the consensus analysis could help get rid of such random noise and detect the systematic errors which are caused by SNPs.

On the simulated data of mitochondrial genome, it is possible to detect SNPs when the coverage is above 6× using the standard pipeline of samtools (Li et al., 2009) and bcftools (Li, 2011)), which is consistent with the conclusion in Zeng et al., 2013. As the number of the implanted SNPs increases, the coverage should increase to ensure all the SNPs to be successfully called. In summary, the detection of the SNPs would become more difficult as the number of SNPs increases. The present experiments demonstrated that in general, 6× coverage would be enough to detect a small number of SNPs.

As a result of the positive outputs of the experiments discussed above, it is believed that the proposed DeepSimulator is the first successful Nanopore simulator that mimics the entire procedure of the Nanopore sequencing. Unlike the previous simulators, which only simulate the reads from the statistical patterns of the real data, the DeepSimulator simulates both the raw electrical current signals and the nucleotide reads.

There are one or more advantages associated with the DeepSimulator. In a first embodiment, the pipeline of the simulator is highly modularized, which is easier to be customized by users. For example, the users can use another basecaller, to replace Albacore, to obtain the reads with the profile of that basecaller. In a second embodiment, because of the modularization of the DeepSimulator when compared with other simulators, it is more likely for the DeepSimulator to keep up with the rapid development of the Nanopore sequencing technology. If one step of the Nanopore sequencing pipeline is updated, it is easy to update the corresponding module of the DeepSimulator without changing the entire pipeline. In a third embodiment, in addition to the final simulated reads, it is also possible to obtain the simulated electrical current signals, which are useful for the development of basecallers and for the benchmarking of signal-level read mappers.

There are two potential applications of the DeepSimulator. First, the DeepSimulator can generate benchmark datasets to evaluate the newly developed methods for Nanopore sequencing data analysis. Unlike the empirical datasets whose ground truth is difficult to obtain, the DeepSimulator can be fully controlled, which makes it a practical complement to the empirical data. Second, as shown in the SNP detection experiments, it can act as a guidance to the empirical experiment by simulating the ideal case.

Figure 7:
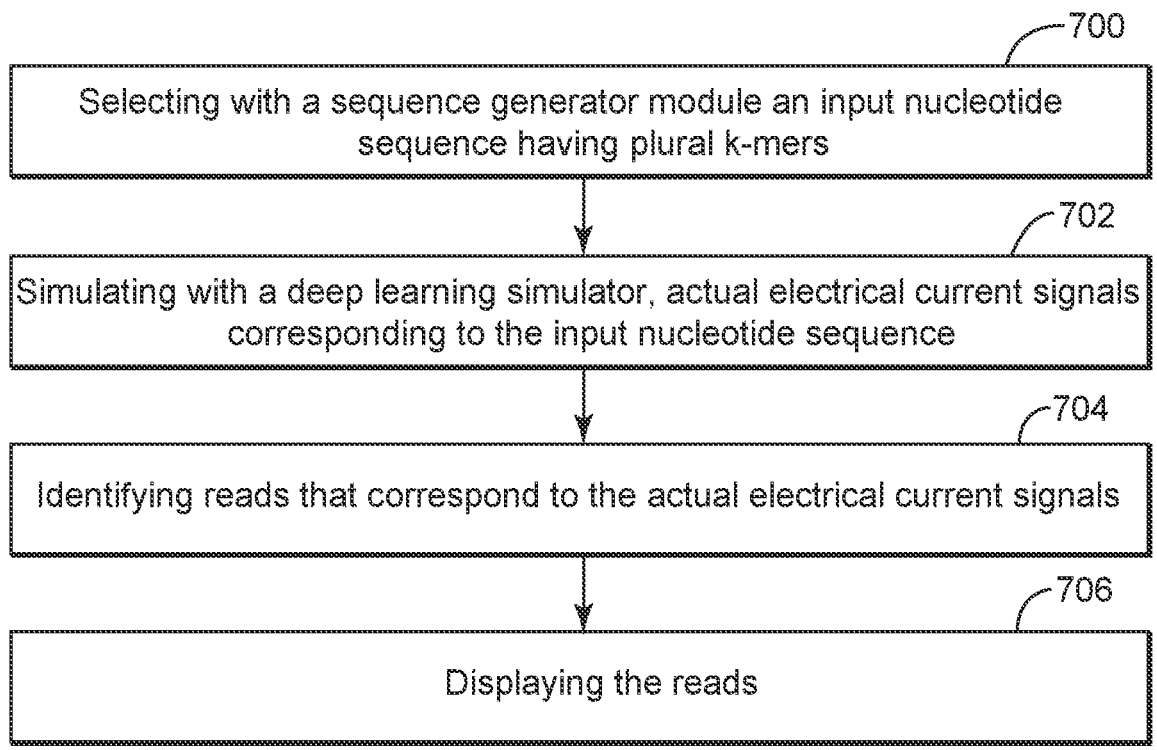
FIG. 7 is a flowchart of a method for sequencing a biopolymer.

A method for sequencing biopolymers is now discussed with regard to FIG. 7. The method includes a step 700 of selecting, with a sequence generator module 104, an input nucleotide sequence 260 having plural k-mers, a step 702 of simulating 702, with a deep learning simulator 100, actual electrical current signals 270 corresponding to the input nucleotide sequence 260, a step 704 of identifying reads 240' that correspond to the actual electrical current signals 270, and a step 706 of displaying the reads 240'. The deep learning simulator 100 includes a context-dependent deep learning model 106A that takes into consideration a position of a k-mer of the plural k-mers on the input nucleotide sequence 206 when calculating a corresponding actual electrical current.

The context-dependent deep learning model calculates transformed signals 550 by using a Bi-LSTM extended Deep Canonical Time Warping, which combines a bi-directional long short-term memory (Bi-LSTM) method with a deep canonical time warping (DCTW) method. In this regard, the context-dependent deep learning model compares two linearly structured data sets having different lengths, and feature dimensionality, wherein the first data set corresponds to the input nucleotide sequence 260 and the second data set corresponds to measured electrical current signals 210.

The method may further include a step of applying a first deep neural network algorithm 408 to the input nucleotide sequence to obtain the first data set, and a step of applying a second deep neural network algorithm 410 to the measured electrical current signals to obtain the second data set, wherein the first and second data sets are in a common space.

In one application, the method may also include a step of applying an objective function to the first and second data sets to temporally align the input nucleotide sequence and the measured electrical current signals, a step of repeating the transformed signals 550, in a signal repeating module 106B, at each position based on a mixture of alpha distributions, to generate the actual electrical current signals 270, and/or a step of adding a random noise to the transformed signals.

In still another application, the method may include a step of using plural different k-mers for each base of the input nucleotide sequence, where the plural different k-mers include a 1-mer, a 3-mer and a 5-mer. The method may further include a step of encoding the bases of the input nucleotide sequence with a one-hot encoding using the plural different k-mers for each base. Furthermore, the method may include a step of randomly selecting a starting position along the input nucleotide and/or a step of selecting a length of a read based on one of three distributions.

Figure 8:
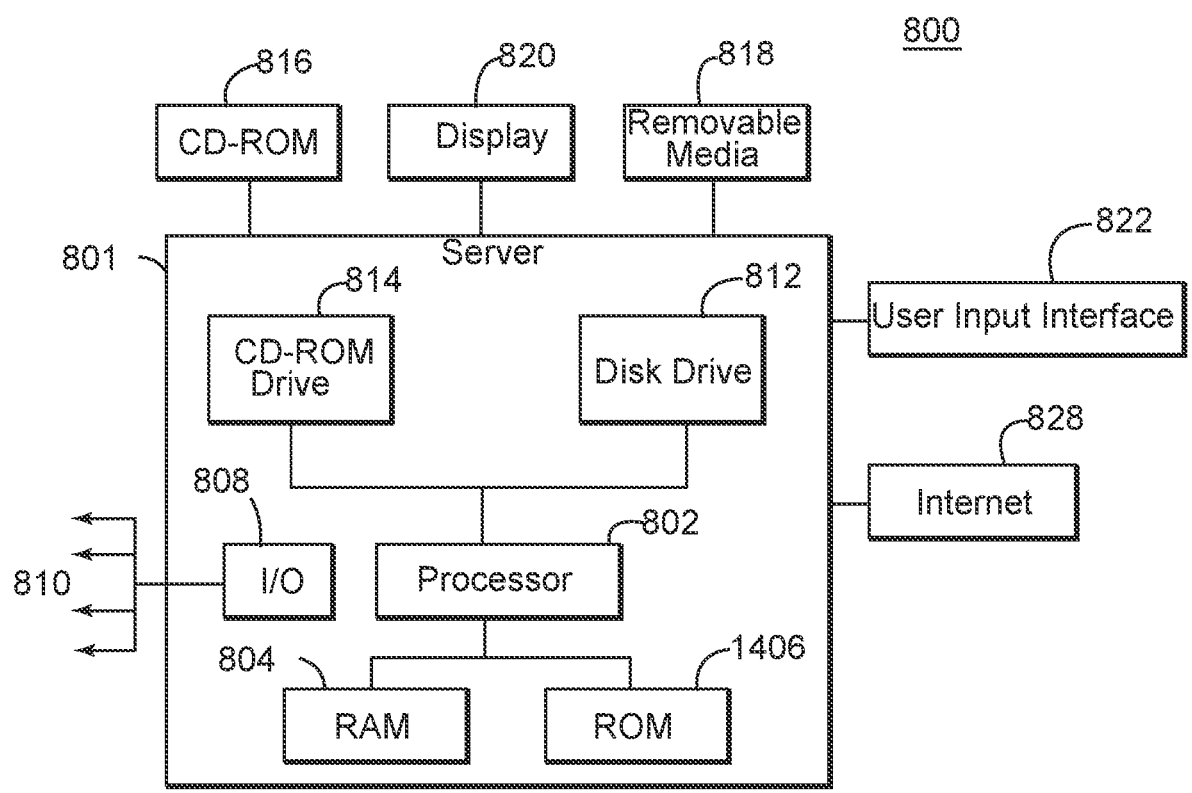
FIG. 8 is a schematic diagram of a computing device that implements the DeepSimulator.

The above-discussed procedures and methods may be implemented in a computing device or controller as illustrated in FIG. 8. Hardware, firmware, software or a combination thereof may be used to perform the various steps and operations described herein. Computing device 800 of FIG. 8 is an exemplary computing structure that may be used in connection with such a system. In one application, the DeepSimulator 100 from FIG. 1 may be implemented in the computing device 800.

Exemplary computing device 800 suitable for performing the activities described in the exemplary embodiments may include a server 801. Such a server 801 may include a central processor (CPU) 802 coupled to a random access memory (RAM) 804 and to a read-only memory (ROM) 806. ROM 806 may also be other types of storage media to store programs, such as programmable ROM (PROM), erasable PROM (EPROM), etc. Processor 802 may communicate with other internal and external components through input/output (I/O) circuitry 808 and bussing 810 to provide control signals and the like. Processor 802 carries out a variety of functions as are known in the art, as dictated by software and/or firmware instructions.

Server 801 may also include one or more data storage devices, including hard drives 812, CD-ROM drives 814 and other hardware capable of reading and/or storing information, such as DVD, etc. In one embodiment, software for carrying out the above-discussed steps may be stored and distributed on a CD-ROM or DVD 816, a USB storage device 818 or other form of media capable of portably storing information. These storage media may be inserted into, and read by, devices such as CD-ROM drive 814, disk drive 812, etc. Server 801 may be coupled to a display 820, which may be any type of known display or presentation screen, such as LCD, plasma display, cathode ray tube (CRT), etc. A user input interface 822 is provided, including one or more user interface mechanisms such as a mouse, keyboard, microphone, touchpad, touch screen, voice-recognition system, etc.

Server 801 may be coupled to other devices, such as a smart device, e.g., a phone, tv set, computer, etc. The server may be part of a larger network configuration as in a global area network (GAN) such as the Internet 828, which allows ultimate connection to various landline and/or mobile computing devices.

The disclosed embodiments provide methods and mechanisms for simulating the entire pipeline of the Nanopore sequencing. It should be understood that this description is not intended to limit the invention. On the contrary, the embodiments are intended to cover alternatives, modifications and equivalents, which are included in the spirit and scope of the invention as defined by the appended claims. Further, in the detailed description of the embodiments, numerous specific details are set forth in order to provide a comprehensive understanding of the claimed invention. However, one skilled in the art would understand that various embodiments may be practiced without such specific details.

Although the features and elements of the present embodiments are described in the embodiments in particular combinations, each feature or element can be used alone without the other features and elements of the embodiments or in various combinations with or without other features and elements disclosed herein.

This written description uses examples of the subject matter disclosed to enable any person skilled in the art to practice the same, including making and using any devices or systems and performing any incorporated methods. The patentable scope of the subject matter is defined by the claims, and may include other examples that occur to those skilled in the art. Such other examples are intended to be within the scope of the claims.

REFERENCES

Abadi, M. (2016). Tensorflow: Learning functions at scale. Acm Sigplan Notices, 51(9), 1-1.

Akaike, H. (1976). Canonical correlation analysis of time series and the use of an information criterion. Mathematics in Science and Engineering, 126, 27-96.

Alipanahi, B., Delong, A., Weirauch, M. T., and Frey, B. J. (2015). Predicting the sequence specificities of dna- and rna-binding proteins by deep learning. Nat Biotechnol, 33(8), 831-8.

Altschul, S. F., Madden, T. L., Schaffer, A. A., Zhang, J., Zhang, Z., Miller, W., and Lipman, D. J. (1997). Gapped blast and psi-blast: a new generation of protein database search programs. Nucleic Acids Res, 25(17), 3389-402.

Baker, E. A. G., Goodwin, S., McCombie, W. R., and Mendivil Ramos, O. (2016). Silico: A simulator of long read sequencing in pacbio and oxford nanopore. bioRxiv, page 76901.

Boza, V., Brejova, B., and Vinar, T. (2017). Deepnano: Deep recurrent neural networks for base calling in minion nanopore reads. PloS one, 12(6), e0178751.

Byrne, A., Beaudin, A. E., Olsen, H. E., Jain, M., Cole, C., Palmer, T., DuBois R. M., Forsberg, E. C., Akeson, M., and Vollmers, C. (2017). Nanopore long-read rnaseq reveals widespread transcriptional variation among the surface receptors of individual b cells. bioRxiv, page 126847.

Dai, H., Umarov, R., Kuwahara, H., Li, Y., Song, L., and Gao, X. (2017). Sequence2vec: A novel embedding approach for modeling transcription factor binding affinity landscape. Bioinformatics.

David, M., Dursi, L. J., Yao, D., Boutros, P. C., and Simpson, J. T. (2016). Nanocall: an open source basecaller for oxford nanopore sequencing data. Bioinformatics, page btw569.

Deamer, D., Akeson, M., and Branton, D. (2016). Three decades of nanopore sequencing. Nature biotechnology, 34(5), 518-525.

Delcher, A. L., Kasif, S., Fleischmann, R. D., Peterson, J., White, O., and Salzberg, S. L. (1999). Alignment of whole genomes. Nucleic Acids Research, 27(11), 2369-2376.

Escalona, M., Rocha, S., and Posada, D. (2016). A comparison of tools for the simulation of genomic next-generation sequencing data. Nat Rev Genet, 17(8), 459-69.

Ester, M., Kriegel, H.-P., Sander, J., and Xu, X. (1996). A density-based algorithm for discovering clusters a density-based algorithm for discovering clusters in large spatial databases with noise. In Proceedings of the Second International Conference on Knowledge Discovery and Data Mining, KDD '96, pages 226-231. AAAI Press.

Graves, A. (2013). Generating sequences with recurrent neural networks. arXivpreprint arXiv:1308.0850.

Graves, A. and Schmidhuber, J. (2005). Framewise phoneme classification with bidirectional lstm and other neural network architectures. Neural Networks, 18(5), 602-610.

Ioffe, S. and Szegedy, C. (2015). Batch normalization: Accelerating deep network training by reducing internal covariate shift. arXiv:1502.03167.

Jain, C., Dilthey, A., Koren, S., Aluru, S., and Phillippy, A. M. (2017a). A fast approximate algorithm for mapping long reads to large reference databases. bioRxiv, page 103812.

Jain, M., Koren, S., Quick, J., Rand, A. C., Sasani, T. A., Tyson, J. R., Beggs, A. D., Dilthey, A. T., Fiddes, I. T., Malla, S., Marriott, H., Miga, K. H., Nieto, T., O'Grady, J., Olsen, H. E., Pedersen, B. S., Rhie, A., Richardson, H., Quinlan, A., Snutch, T. P., Tee, L., Paten, B., Phillippy, A. M., Simpson, J. T., Loman, N. J., and Loose, M. (2017b). Nanopore sequencing and assembly of a human genome with ultra-long reads. bioRxiv.

Kingma, D. and Ba, J. (2014). Adam: A method for stochastic optimization. arXivpreprint arXiv:1412.6980.

Koren, S., Walenz, B. P., Berlin, K., Miller, J. R., Bergman, N. H., and Phillippy, A. M. (2017). Canu: scalable and accurate long-read assembly via adaptive k-mer weighting and repeat separation. Genome Res, 27(5), 722-736.

Lee, H., Gurtowski, J., Yoo, S., Marcus, S., McCombie, R. W., and Schatz, M. (2014). Error correction and assembly complexity of single molecule sequencing reads. BioRxiv, page 6395.

Li, H. (2011). A statistical framework for snp calling, mutation discovery, association mapping and population genetical parameter estimation from sequencing data. Bioinformatics, 27(21), 2987-2993.

Li, H. (2016). Minimap and miniasm: fast mapping and de novo assembly for noisylong sequences. Bioinformatics, 32(14), 2103-2110.

Li, H. (2017). Minimap2: fast pairwise alignment for long nucleotide sequences. arXiv.

Li, H., Handsaker, B., Wysoker, A., Fennell, T., Ruan, J., Homer, N., Marth, G., Abecasis, G., Durbin, R., and (2009). The sequence alignment/map format and samtools. Bioinformatics, 25(16), 2078-2079.

Li, Y., Wang, S., Umarov, R., Xie, B., Fan, M., Li, L., and Gao, X. (2017). Deepre: sequence-based enzyme ec number prediction by deep learning. Bioinformatics.

Lu, H., Giordano, F., and Ning, Z. (2016). Oxford nanopore minion sequencing and genome assembly. Genomics, proteomics & bioinformatics, 14(5), 265-279.

MacLean, D., Jones, J. D. G., and Studholme, D. J. (2009). Application of 'next-generation' sequencing technologies to microbial genetics. Nature Reviews Microbiology, 7(4), 287-296.

Metzker, M. L. (2010). Sequencing technologies—the next generation. Nature reviews. Genetics, 11(1), 31.

Salvador, S. and Chan, P. (2007). Toward accurate dynamic time warping in linear time and space. Intell. Data Anal., 11(5), 561-580.

Simpson, J. T., Workman, R. E., Zuzarte, P., David, M., Dursi, L., and Timp, W. (2017). Detecting dna cytosine methylation using nanopore sequencing. nature methods, 14(4), 407-410.

Sović, I., ˇSikić, M., Wilm, A., Fenlon, S. N., Chen, S., and Nagarajan, N. (2016). Fast and sensitive mapping of nanopore sequencing reads with graphmap. Nature communications, 7, 11307.

Stewart, J. B. and Chinnery, P. F. (2015). The dynamics of mitochondrial dna heteroplasmy: implications for human health and disease. Nature Reviews Genetics, 16(9), 530-542.

Stoiber, M. and Brown, J. (2017). Basecrawller: Streaming nanopore basecalling directly from raw signal. bioRxiv, page 133058.

Swain, M. J. and Ballard, D. H. (1991). Color indexing. Int. J. Comput. Vision, 7(1), 11-32.

Trigeorgis, G., Nicolaou, M. A., Zafeiriou, S., and Schuller, B. W. (2016). Deep canonical time warping. In Proceedings of the IEEE Conference on Computer Vision and Pattern Recognition, pages 5110-5118.

Vaser, R., Sovic, I., Nagarajan, N., and Sikic, M. (2017). Fast and accurate de novo genome assembly from long uncorrected reads. Genome Research.

Yang, C., Chu, J., Warren, R. L., and Birol, I. (2017). Nanosim: nanopore sequence read simulator based on statistical characterization. GigaScience, 6(4), 1-6.

Zeng, F., Jiang, R., and Chen, T. (2013). Pyrohmmvar: a sensitive and accurate method to call short indels and snps for ion torrent and 454 data. Bioinformatics, 29(22), 2859-2868.

What is claimed is:

1. A method for simulating reads for a sequencing technology of biopolymers that uses nanopores, the method comprising:
generating, with a sequence generator module, an input nucleotide sequence having plural k-mers, wherein the input nucleotide sequence satisfies coverage and length distribution associated with the sequencing technology that uses the nanopores;
simulating with a deep learning simulator, actual electrical current signals corresponding to the input nucleotide sequence;
identifying reads that correspond to the actual electrical current signals; and
displaying the reads,
wherein the deep learning simulator includes a context-dependent deep learning model that takes into consideration a position of a k-mer of the plural k-mers on the input nucleotide sequence when calculating a corresponding actual electrical current.

2. The method of claim 1, wherein the context-dependent deep learning model calculates transformed signals by using a Bi-LSTM extended Deep Canonical Time Warping, which combines a bi-directional long short-term memory (Bi-LSTM) method with a deep canonical time warping (DCTW) method.

3. The method of claim 2, wherein the context-dependent deep learning model compares two linearly structured data sets having different lengths, and feature dimensionality, wherein the first data set corresponds to the input nucleotide sequence and the second data set corresponds to measured electrical current signals.

4. The method of claim 3, further comprising:
applying a first deep neural network algorithm to the input nucleotide sequence to obtain the first data set; and
applying a second deep neural network algorithm to the measured electrical current signals to obtain the second data set,
wherein the first and second data sets are in a common space.

5. The method of claim 4, further comprising:
applying an objective function to the first and second data sets to temporally align the input nucleotide sequence and the measured electrical current signals.

6. The method of claim 2, further comprising:
repeating the transformed signals, in a signal repeating module, at each position based on a mixture of alpha distributions, to generate the actual electrical current signals.

7. The method of claim 6, further comprising:
adding a random noise to the transformed signals.

8. The method of claim 1, wherein the plural different k-mers include a 1-mer, a 3-mer and a 5-mer.

9. The method of claim 1, further comprising:
encoding the bases of the input nucleotide sequence with a one-hot encoding using the plural different k-mers for each base.

10. The method of claim 1, wherein the step of selecting further comprises:
randomly selecting a starting position along the input nucleotide.

11. The method of claim 10, further comprising:
selecting a length of a read based on one of three distributions.

12. The method of claim 1, further comprising:
using plural different k-mers for each base of the input nucleotide sequence.

13. A computing device for simulating reads for a sequencing technology of biopolymers, the computing device comprising:
a processor for,
generating, with a sequence generator module, an input nucleotide sequence having plural k-mers, wherein the input nucleotide sequence satisfies coverage and length distribution associated with the sequencing technology that uses the nanopores;
simulating with a deep learning simulator, actual electrical current signals corresponding to the input nucleotide sequence; and
identifying reads that correspond to the actual electrical current signals; and
a display for displaying the reads,
wherein the deep learning simulator includes a context-dependent deep learning model that takes into consideration a position of a k-mer of the plural k-mers on the input nucleotide sequence when calculating a corresponding actual electrical current.

14. The device of claim 13, wherein the context-dependent deep learning model calculates transformed signals by using a Bi-LSTM extended Deep Canonical Time Warping, which combines a bi-directional long short-term memory (Bi-LSTM) method with a deep canonical time warping (DCTW) method.

15. The device of claim 14, wherein the context-dependent deep learning model compares two linearly structured data sets having different lengths, and feature dimensionality, wherein the first data set corresponds to the input nucleotide sequence and the second data set corresponds to measured electrical current signals.

16. The device of claim 15, wherein the processor is further configured to:
apply a first deep neural network algorithm to the input nucleotide sequence to obtain the first data set; and
apply a second deep neural network algorithm to the measured electrical current signals to obtain the second data set,
wherein the first and second data sets are in a common space.

17. The device of claim 16, wherein the processor is further configured to:
apply an objective function to the first and second data sets to temporally align the input nucleotide sequence and the measured electrical current signals.

18. The device of claim 14, wherein the processor is further configured to:
repeat the transformed signals, in a signal repeating module, at each position based on a mixture of alpha distributions, to generate the actual electrical current signals.

19. The device of claim 18, wherein the processor is further configured to:
add a random noise to the transformed signals.

20. A non-transitory computer readable medium including computer executable instructions, wherein the instructions, when executed by a processor, implement instructions for simulating reads for a sequencing technology of biopolymers, the instructions comprising:
generating, with a sequence generator module, an input nucleotide sequence having plural k-mers, wherein the input nucleotide sequence satisfies coverage and length distribution associated with the sequencing technology that uses the nanopores;
simulating with a deep learning simulator, actual electrical current signals corresponding to the input nucleotide sequence (260);
identifying reads that correspond to the actual electrical current signals; and
instructing a display to display the reads,
wherein the deep learning simulator includes a context-dependent deep learning model that takes into consideration a position of a k-mer of the plural k-mers on the input nucleotide sequence when calculating a corresponding actual electrical current.

* * * * *